United States Patent [19]

Sunahara et al.

[11] 4,099,871

[45] Jul. 11, 1978

[54] METHOD AND APPARATUS FOR DETERMINATION OF ACTIVATED SLUDGE VOLUME INDEX

[75] Inventors: Hiroshi Sunahara, Seto; Yutaka Ishihara, Anjyo; Kazuhiko Tanaka, Nagoya; Yuko Morimoto, Kyoto, all of Japan

[73] Assignees: Agency of Industrial Science and Technology, Tokyo; Yanagimoto Manufacturing Co., Ltd., Kyoto, both of Japan

[21] Appl. No.: 698,319

[22] Filed: Jun. 22, 1976

[30] Foreign Application Priority Data

Jun. 24, 1975 [JP] Japan .................................. 50-78236

[51] Int. Cl.² ...................... G01N 21/24; B01D 21/02
[52] U.S. Cl. ..................................... 356/73; 210/143; 356/197; 356/208
[58] Field of Search ...................... 356/36, 70, 73, 197, 356/208, 206, 207; 250/564, 573, 575, 577; 73/61 R; 210/96 R, 143

[56] References Cited

U.S. PATENT DOCUMENTS

| 2,725,782 | 12/1955 | Worley ............................... 356/208 |
| 3,504,185 | 3/1970 | Zweig et al. ..................... 324/71 CP |
| 3,518,437 | 6/1970 | Riggs .................................. 356/207 |
| 3,715,761 | 2/1973 | Drekter et al. ....................... 356/39 |
| 3,972,614 | 8/1976 | Johansen et al. ..................... 356/36 |

FOREIGN PATENT DOCUMENTS

720,055   12/1954   United Kingdom ................. 356/208

OTHER PUBLICATIONS

Briggs, R., "Continuous Recording of Suspended Solids in Effluents", J. Sci. Instrum., vol. 39, 1962, pp. 2-7.
Swanwick, K. H., "Instrumental Measurement of Suspended Solids for Activated-Sludge Plant Control", Paper #29 of Progress in Water Technology, vol. 6, Instrumentation Control and Automation for Waste-Water Treatment Systems, Edited by Andrews et al., Pergamon Press, 1974, pp. 221-230.

*Primary Examiner*—John K. Corbin
*Assistant Examiner*—Wm. H. Punter
*Attorney, Agent, or Firm*—Oblon, Fisher, Spivak, McClelland & Maier

[57] ABSTRACT

Automatic determination of the activated sludge volume index by use of a single sample is accomplished by a method which comprises placing in a test cell a mixed liquor of activated sludge sampled at the aerator outlet or at the final settler, automatically determining the concentration of activated sludge and the sedimentation rate of activated sludge by optical means and calculating the activated sludge volume index by subjecting the found values of activated sludge concentration and activated sludge sedimentation rate to an arithmetic circuit.

4 Claims, 5 Drawing Figures

METHOD AND APPARATUS FOR DETERMINATION OF ACTIVATED SLUDGE VOLUME INDEX

BACKGROUND OF THE INVENTION

This invention relates to a method and an apparatus for the determination of activated sludge volume index in the activated sludge process. To be more particular, the present invention relates to a method for automatic determination of the activated sludge volume index of a mixed liquor of activated sludge obtained in the form of a single sample in the aeration state of the activated sludge process employed for the treatment of municipal sewage, organic industrial wastewater, etc. and to an apparatus for practicing said method.

In the activated sludge process, the activity of biodegration of organic pollutants is effected preponderantly in the form of a biochemical reaction which is caused in the aerator. The efficiency of the treatment, therefore, depends upon the activity, mass of the activated sludge reacted with the pollutants and optimum concentration of dissolved oxygen in the aerator. For separation of activated sludge and treated water in the final settler, the activated sludge volume index (hereinafter referred to as S.V.I.) is also utilized as the criterion for the efficient and rapid separation of the activated sludge from the treated water. Accordingly, the S.V.I. proves to constitute an important criterion in the operation of the activated sludge process. The S.V.I. is expressed in the number of ml's (volume) which is assumed by 1 g of the suspended solids in the sedimented sludge obtained by subjecting the mixed liquor of activated sludge in the aerator to sedimentation for 30 minutes. This value has heretofore been determined by a method which comprises the steps of taking fixed-volume samples of the mixed liquor of activated sludge prior to its entry into the final settler, filtering one sample through a filter paper No. 6 (standard type for quantitative analysis), drying the activated sludge lodged on the surface of the filter paper, weighing the dry activated sludge to find the concentration of activated sludge (%), separately allowing another sample to stand at rest for 30 minutes, finding the volume of the sedimented activated sludge, calculating the percentage of the found volume based on the volume of the original sample, namely the sedimentation rate (%) of the activated sludge, and performing a calculation involving said concentration of activated sludge and said sedimentation rate of activated sludge in accordance with the following formula (1).

$$S.V.I. = \frac{\text{Sedimentation rate (\%) of activated sludge}}{\text{Concentration (\%) of activated sludge}} \quad (1)$$

The method heretofore adopted for the determination of S.V.I. is complicated as has already been pointed out and it has been practiced substantially in a manual operation. Thus, it normally takes as much as four hours to determine the concentration and sedimentation rate of a sample of activated sludge and calculate the S.V.I. from the determined values. Moreover, the values of S.V.I. obtained by this method are subject to a fairly wide range of personal error even when the determination is carried out on the same samples. With this method, therefore, it has been difficult to obtain accurate S.V.I. values quickly. Furthermore, this method has been unable to determine both the sedimentation rate of activated sludge and the concentration of activated sludge for the same single sample, because the former is obtained by allowing the sample to stand for a prescribed length of time, finding the volume of suspended solids and calculating the percentage of the found volume based on the volume of the original sample while the latter is obtained by filtering the sample, drying the filtration residue and weighing the dry residue.

Recently, methods for automatic continuous determination of the concentration of activated sludge and the sedimentation rate of activated sludge have been proposed. (A method for the determination of the concentration of activated sludge is disclosed in U.S. Pat. No. 3,893,333, for example.) These methods are intended to determine the concentration of activated sludge and the sedimentation rate of activated sludge separately of each other. None of them is capable of automatically determining the S.V.I. of a single sample of mixed liquor of activated sludge.

An object of the present invention is to provide a method and an apparatus for S.V.I. determination, which method and apparatus are readily capable of automatically determining the concentration of activated sludge and the sedimentation rate of activated sludge of a single sample of mixed liquor of activated sludge, rapidly calculating the S.V.I. automatically from the determined values, recording the data resulting from said calculation and electrically displaying the recorded data or converting said data into electric signals to transmit to a remote place.

SUMMARY OF THE INVENTION

To accomplish the object described above according to the present invention, the method for the automatic determination of the S.V.I. comprises the steps of collecting in a test cell a sample of mixed liquor of activated sludge at the outlet of the aerator or the inlet of the final settler serving to separate the activated sludge from the treated water in the activated sludge process, determining the concentration of activated sludge and the sedimentation rate of the activated sludge of the sample in the test cell by the use of a transmitting light detector and a scattering light detector, calculating the activated sludge volume index by subjecting the determined concentration of activated sludge and the sedimentation rate of activated sludge to an arithmetic circuit and, as occasion demands, recording the concentration of activated sludge, the sedimentation rate, the sedimentation curve of activated sludge, and the S.V.I., and electrically displaying the recorded data or converting the data into electric signals and transmitting the signals to a remote place.

Further, the apparatus to be used for practicing the method of this invention comprises sampling means adapted to collect in a test cell a sample of mixed liquor of activated sludge and, upon completion of the determination, return the used sample from said test cell to the place of sampling, sample preparation means adapted to measure the sample within the test cell and introduce air to agitate the sample uniformly, means for determination of activated sludge adapted to admit light through the sample in the test cell and determine the concentration of activated sludge from the logarithm of the ratio of the intensity of scattering light to the intensity of transmitting light, means for determination of sedimentation rate of activated sludge adapted to allow the sample in the test cell to stand at rest for a prescribed length of time and trace and determine the rate of sedimentation of activated sludge, test cell washing means adapted to discharged the used sample from within the test cell, introduce the washing water into the cell interior and give a washing to the cell interior, arithmetic means adapted to calculate the S.V.I. on the basis of the value from said means for determination of the concentration of activated sludge and the value from said means for determination of the sedimentation rate of activated sludge, data display and transmission means adapted to record and display the values of said concentration of activated sludge, sedimentation rate and sedimentation curve of activated sludge and S.V.I. or converting said data into electric signals and transmitting said signals, and automatically operated programming means for issuing operation commands automatically and continuously to the various means described above.

The determination of the S.V.I. described above can wholly be carried out automatically, enabling the operation of determination itself to be expedited and permitting the S.V.I. to be obtained accurately with absolutely no dispersion in the results of the determination.

Since the concentration of activated sludge and the sedimentation rate of activated sludge are obtained from a single sample, the S.V.I. represents the value of a particular sample and therefore proves to be accurate.

The other objects and characteristic features of the present invention will become apparent from the description to be given in further detail herein below with reference to the accompanying drawing.

BRIEF DESCRIPTION OF THE DRAWINGS

FIG. 1 is a schematic diagram illustrating a sampling means, a sample preparation means and a test cell washing means, FIG. 2 is a schematic diagram illustrating a means for determination of the concentration of activated sludge, a means for determination of the sedimentation rate of activated sludge, an arithmetic means and a data display and transmission means, and FIG. 3 is an explanatory diagram illustrating the method for determination of the concentration of activated sludge.

DESCRIPTION OF THE PREFERRED EMBODIMENTS

The apparatus for the determination of S.V.I. according to the present invention comprises sampling means, sample preparation means, means for determination of the concentration of activated sludge, means for determination of the sedimentation rate of activated sludge, test cell washing means, arithmetic means, means for the data display and transmission and automatic process control means. The correlation and operation of these means will now be described with reference to the accompanying drawing.

Figure 1:
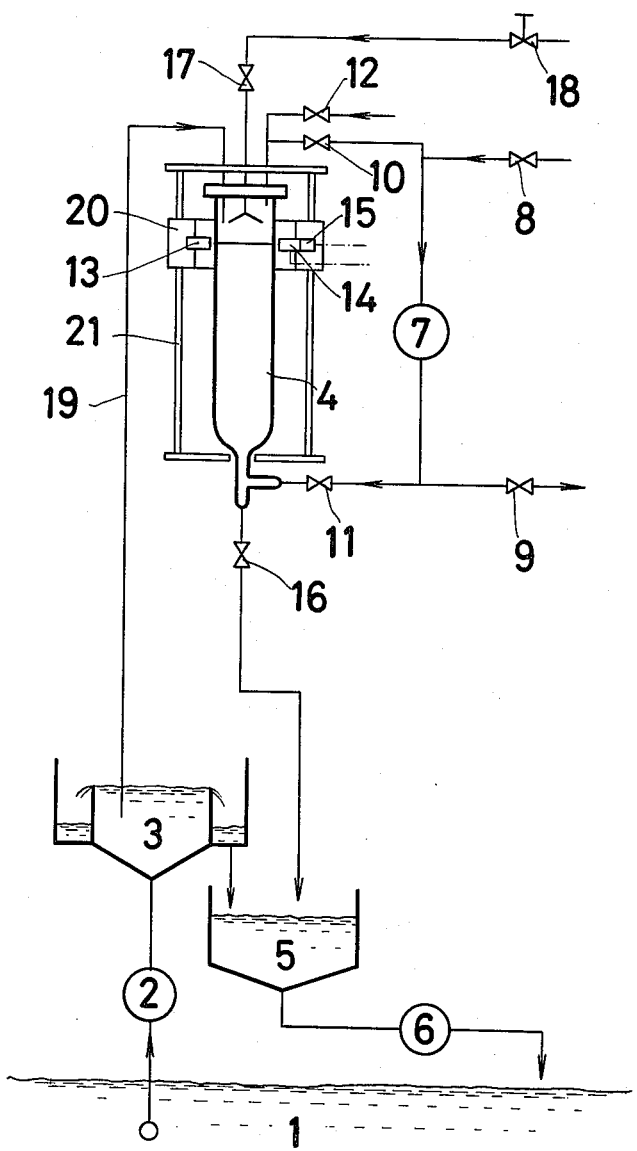
FIGS. 1-3 illustrate one preferred embodiment of the apparatus for practicing the method of this invention for the determination of S.V.I.

Referring to FIG. 1, the sampling means is intended to introduce a fixed volume of sample into a test cell. The sample 1 (mixed liquor of activated sludge) taken at the outlet of the aerator (not illustrated) or at the inlet of the final settler (not illustrated) serving to separate the activated sludge from the treated water is forwarded by a pump 2 into an overflowing storage tank 3. The liquor overflowing said storage tank 3 again overflows a returning storage tank 5. The liquor which overflows this returning storage tank 5 is returned via a pump 6 to the original place of sampling. As a pneumatic pump 7 is driven, solenoid valves 11, 12, 16 and 17 are closed and solenoid valves 8, 9 and 10 are opened. As a result, the air within the test cell 4 is drawn out by the pneumatic pump 7 and discharged via the solenoid valve 9, leaving the interior of the test cell in a state of reduced pressure. The sample within the storage tank 3, therefore, is introduced via the pipe 19 into the test cell interior. At a prescribed level corresponding to the upper section of the test cell 4, a light source 13 and a transmitting light detector 15 are supported in position by a support 20 vertically movable through pillars 21 piercing therethrough in such way that the optical axis thereof passes the center of said test cell 4. As the liquid surface of the sample placed inside the test cell intercepts the light from the light source 13 and the luminous intensity sensed on the transmitting light detector 15 is consequently lowered, the solenoid valve 10 is closed with the result that a fixed amount of sample is metered out and introduced into the test cell 4. In this case, the air introduced from the solenoid valve 8 is discharged through the solenoid valve 9.

The sample preparation means is intended to uniformize the sample of mixed liquor of activated sludge held in the test cell. As a fixed amount of sample is received in the test cell 4, the solenoid valve 9 closes itself and the solenoid valve 11 opens to admit the air from the solenoid valve 8 into the lower section of the test cell 4, from which the air is allowed to bubble up the sample to aerate the interior of the test cell 4. The air bubbles which have reached the top of the cell interior are discharged through the solenoid valve 12. The time for this aeration generally ranges from 2 to 3 seconds. After the aeration, the solenoid valve 11 is closed and the pneumatic pump 7 is stopped in order that fine air bubbles persisting inside the test cell 4 may float up and depart from the cell interior.

Figure 2:
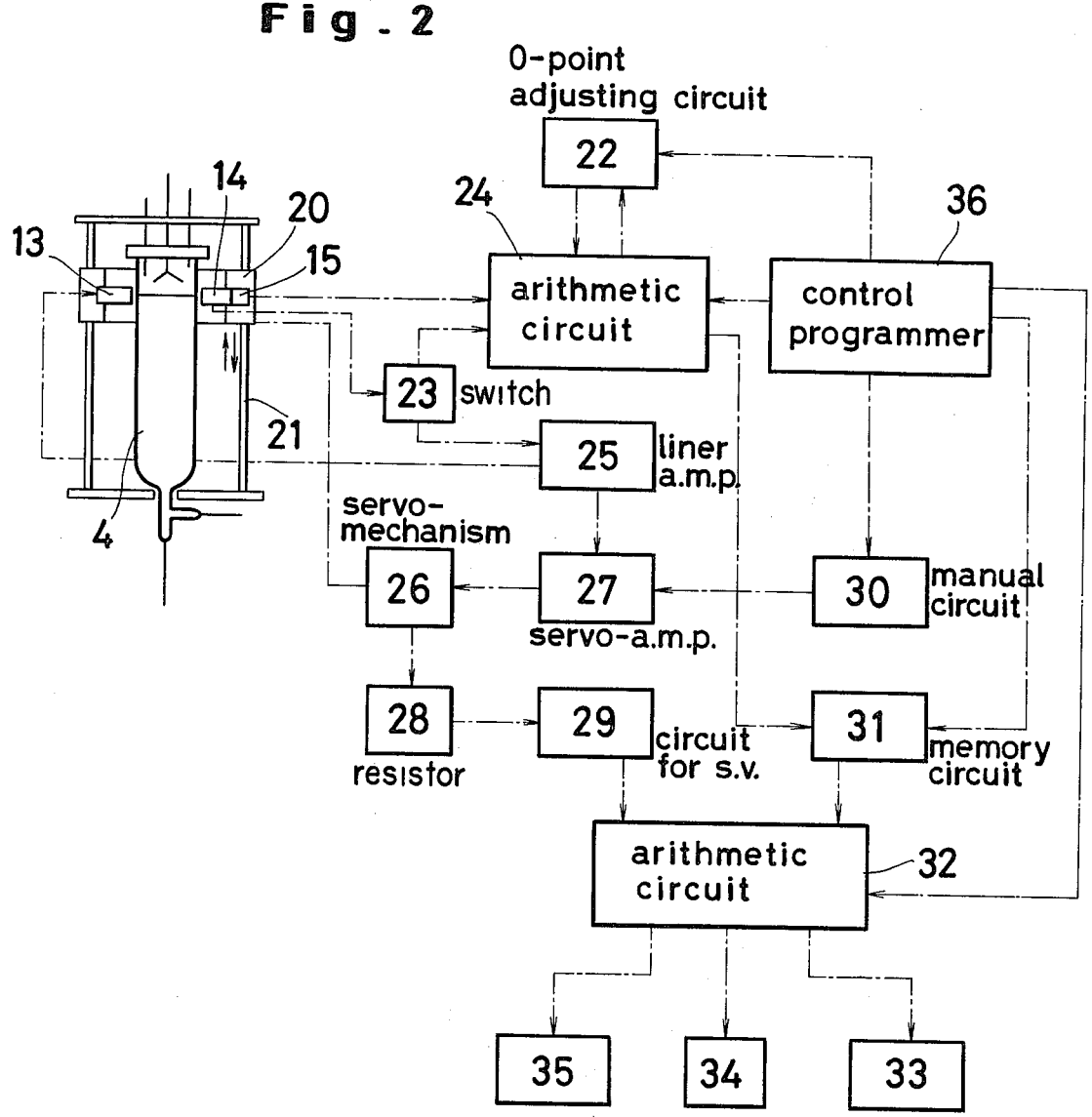
Figure 3:
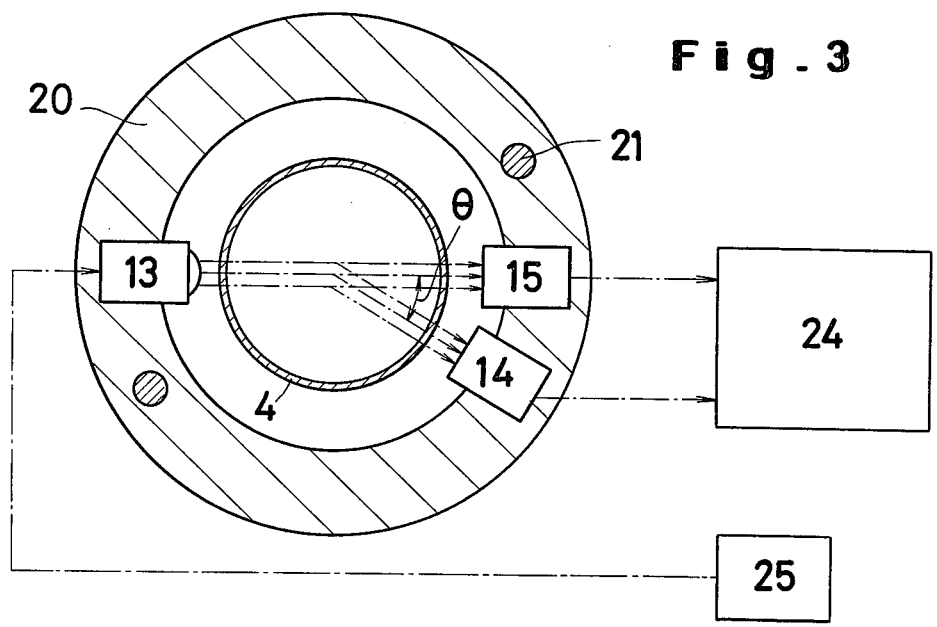

The means for determination of the concentration of activated sludge is an optical detector which consists of a light source 13, a transmitting light detector 15 and a scattering light detector 14. As illustrated in FIG. 3, the scattering light detector 14 is disposed in such way that the optical axis thereof and the common optical axis of the light source 13 and the transmitting light detector 15 intersect each other at the center of the cell 4 at an angle of from about 5° to about 45° in one common optical plane. It is held in position in conjunction with the light source and the transmitting light detector by the support 20 which is adapted to be moved vertically along the test cell by means of the signal from the balancing servomechanism 26 (FIG. 2).

On the basis of the intensity of transmitting light $I_T$ and the intensity of scattering light $I_S$ determined by the transmitting light detector and the scattering light detector disposed as described above, the concentration of activated sludge (M.L.S.S.) is calculated in accordance with the formula (2) shown below.

$$M.L.S.S. = k \log I_S/I_T \quad (2)$$

In the formula, $k$ represents a constant.

Generally, the concentration of activated sludge is determined on the basis of either transmitting light or scattering light. If the sample happens to be colored, however, this determination is affected by the color of the sample. According to the present invention, since the determination relies on the calculation of the logarithmic ratio between the intensity of scattering light and that of transmitting light as described above, possible effect of the color of the sample is eliminated substantially completely. Moreover, the angle at which the optical axis of transmitting light and that of scattering light intersect each other can be selected in the range of from the angle at which the direct light from the light source is not allowed to impinge upon the scattering light detector (about 5° by taking the safety factor into consideration) to 45°. The determination of the concentration is affected very little by the variation of this angle.

As the sample held within the test cell 4 has undergone the aeration treatment, the support 20 on which the light source 13, the transmitting light detector 15 and the scattering light detector 14 are disposed is immediately lowered to a position corresponding to about half of the height of the test cell 4 to permit determination of the intensity of transmitting light $I_T$ and that of scattering light $I_S$ of the sample. The values of intensity thus determined are forwarded to an optical arithmetic circuit 24, in which the logarithmic ratio of the intensity of scattering light $I_S$ and that of transmitting light $I_T$ is calculated in accordance with the formula (2). The output of this arithmetic circuit 24 is memorized as the concentration of activated sludge in a memory circuit 31.

The means for determination of the sedimentation rate of activated sludge is intended to determine the degree to which the activated sludge contained in the sample held inside the test cell sediments during a fixed length of time. The optical detector is positioned at a level corresponding to the upper section of the test cell to find the height of the sample. Then, the light from the light source 13 is allowed to pass through the sample and is then detected by the transmitting light detector 15. The output of the detector 15 is sent by a changeover switch 23 to a linear amplifier 25 to be amplified. The amplified output is compared in a servoamplifier 27 with the value corresponding to the sedimentation interface set in advance. If the amplified output has a larger value than said set value, i.e. if the transmitted light is brighter than the preset standard intensity, a signal is issued to the balancing servomechanism 26, causing the support 20 to go down. The changing sedimentation interface of the sample is automatically traced by thus making the comparison of the output of the detector 15 with the present level continuously. The time for the determination of sedimentation rate is set by the timer which is situated inside the automatic test control programmer 36 of the automatic process control means. The support 20 is interlocked with a variable resistor 28 and serves to electrically detect the volume of activated sludge in accordance with the position at which the support 20 is held in position during the preset time interval. In the circuit 29 for determination of activated sludge sedimentation rate, the sedimentation rate of activated sludge (S.V.) is calculated on the basis of the height of the sample and the position at which the support 20 is held in position. The result of this calculation is forwarded to the data processing arithmetic circuit 32. After the concentration of activated sludge (M.L.S.S.) and the sedimentation rate of activated sludge (S.V.) have been determined as described above, the test cell is washed by the test cell washing means (FIG. 1). First, the pinch valve 16 is opened to cause the sample held inside the test cell to be released into the returning storage tank 5. Thereafter, the solenoid valves 9 and 10 and the pinch valve 16 are closed. Tap water which has its pressure adjusted by the tap water adjusting valve 18 enters the test cell 4 as the solenoid valve 17 is opened. The pneumatic pump 7 is actuated and the solenoid valves 8 and 11 are opened to admit air through the lower section of the test cell 4 and cause a forced flow of the washing water, with the result that the matter adhering to the inner wall surface of the test cell will be washed off. Subsequently, the solenoid valves 11 and 17 are closed and the pinch valve 16 is closed, allowing the washings inside the cell 4 to be discharged into the returning storage tank 5. Said washing operation, washing time and frequency of washing are set in advance in the control programmer 36 which issues commands to suit the occasion.

To avoid possible degradation of performance of the light source 13, the transmitting light detector 15 and the scattering light detector 14 at the final stage of the test cell washing operation, the output of said optical detector obtained at the moment that the washing water enters the test cell 4 is forwarded from the optical arithmetic circuit 24 to the zero point adjusting circuit 22 to be adjusted so that the concentration of activated sludge at this time becomes zero.

The arithmetic means is intended to calculate the S.V.I. on the basis of the concentration of activated sludge and the sedimentation rate of activated sludge. The data of the concentration of activated sludge stored in the memory circuit 31 and those on the sedimentation rate of activated sludge obtained at the circuit 29 are respectively forwarded to the data processing arithmetic circuit 32, wherein the S.V.I. is calculated from these data in accordance with the formula (1).

The automatic data display and transmission means is intended to cause these data, i.e., those of the concentration of activated sludge and those of the sedimentation rate of activated sludge received as the input signal in the data processing arithmetic circuit 32 and those of the S.V.I. calculated in the arithmetic circuit 32, to be recorded in the recorder 33, displayed on the digital panel meter 34 or transmitted to a remote place. For the purpose of this transmission, the data are converted into electric signals by means of the converter-transmission 35. The recording or displaying of data or the transmission of converted data is automatically effected by a command from the automatic test control programmer 36.

The automatic process control means consists of said automatic test control programmer 36 and manual test control circuit 30. The automatic test control programmer 36 issues sequential commands to the sampling means, the sample preparation means, the means for determination of the concentration of activated sludge, the means for determination of the sedimentation rate of activated sludge, the test cell washing means, the arithmetic means and the data display and transmission means to cause the various functions described above to be effected automatically. By contrast, the manual test control circuit 30 is used to permit sample collection, sample preparation, determination of the concentration of activated sludge, determination of the sedimentation rate of activated sludge, etc. to be carried out manually.

The S.V.I. is an important item of control in the treatment of wastewater by the activated sludge process, with a view to faithful observation of the effluence standards established by the Water Pollution Prevention Law. Said treatment of wastewater is desired to be carried out constantly under the most advantageous conditions through continuous determination of said index. The determination by the conventional manual method is slow and admits of a considerable range of personal error in the data consequently obtained, so that necessary corrective measures to be taken for proper treatment cannot be made in time and continuance of the treatment under the optimum conditions proves to be barely practicable.

The method and apparatus for the automatic determination of the S.V.I. according to this invention permit the determination to be carried out automatically and continuously with high accuracy and to be completed in a matter of 40 to 50 minutes, enabling the operator to make early detection of abnormality of operation, take prompt measures for proper management and carry through the operation under the most advantageous conditions. Thus, the present invention makes a great contribution to the optimum operational management of wastewater treatment by the activated sludge process.

Now the present invention will be described with reference to preferred embodiments. It should be noted, however, that the present invention is not limited to these samples.

EXAMPLE 1

In the final settler of the wastewater treatment system utilizing the activated sludge process at an oil refinery, the returned sludge separated from the treated water was sampled and tested for concentration of activated sludge by a manual method.

Then, this sample was diluted with water to a total of nine concentrations. One of the dilute samples was placed in a test cell and aerated by agitation given for five seconds with air introduced upwardly from the lower section of the test cell. Thereafter, the optical detector was lowered to a level corresponding to half of the height of the test cell and the light source was operated to emit the light in the direction of the transmitting light detector and the scattering light detector. The scattering light detector was disposed in such a relative position that the optical axis thereof formed an angle of 30° with the optical axis between the light source and the transmitting light detector. The numerical values of the results of determination by the transmitting light detector and the scattering light detector are forwarded via the determination circuit to the memory circuit for the concentration of activated sludge to undergo an arithmetic operation. The interval between the time the sample was introduced into the test cell and the time the results of determination were obtained was about 10 seconds.

After the determination, the sample was withdrawn from the test cell and the test cell was washed three times by the procedure described in the specification. Then, another diluted sample was introduced into the test cell and subjected to determination of the concentration of activated sludge by the same procedure as described above. All the remaining diluted samples were subjected one another to determination of the concentration of activated sludge by the same procedure.

Figure 4:
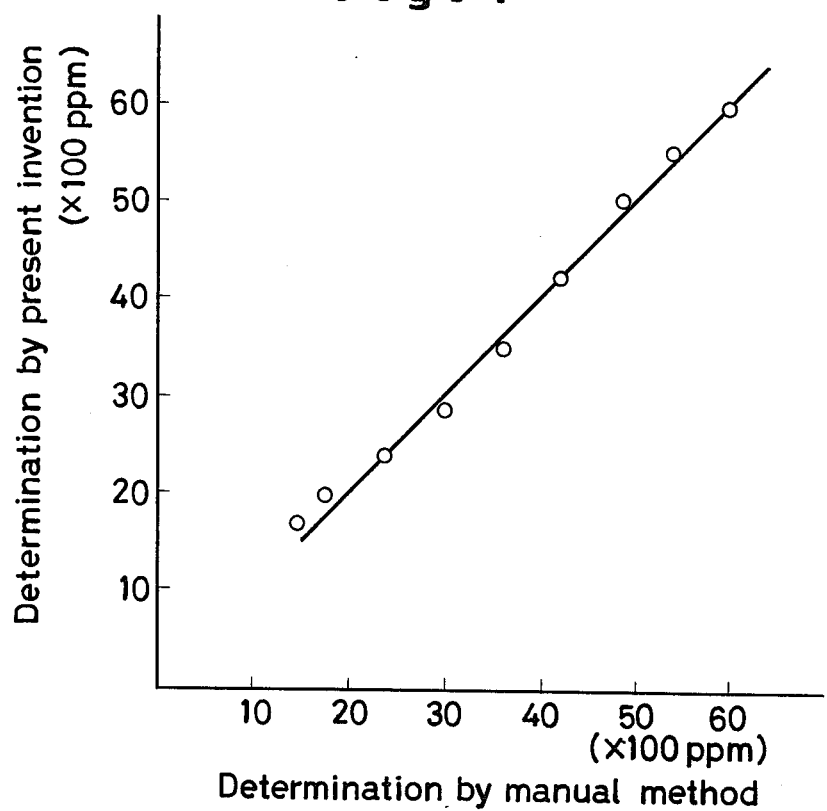
FIG. 4 is a graph comparing the S.V.I. obtained by the method of this invention and the S.V.I. obtained by the conventional manual method, both from one and the same sample of mixed liquor of activated sludge.

The results thus obtained were as indicated by the graph of FIG. 4.

In the graph, the horizontal axis represents the results of determination by the manual method and the vertical axis represents the results of determination by the method of this invention.

In the case of a sample of which the concentration of activated sludge was 2,000 ppm, the value obtained by the manual method was about 2,000 ppm and the value obtained by the method of this invention was about 1,800 ppm. In the case of a sample of which the concentration of activated sludge was 5,000 ppm, the value obtained by the manual method was about 5,100 ppm and the value obtained by the method of this invention was about 4,900 ppm. The values thus determined were approximately in agreement with the true values (indicated by a slanted line), indicating that the method for the determination of the concentration of activated sludge by the present invention can be used for the automatic determination of S.V.I.

EXAMPLE 2

Figure 5:
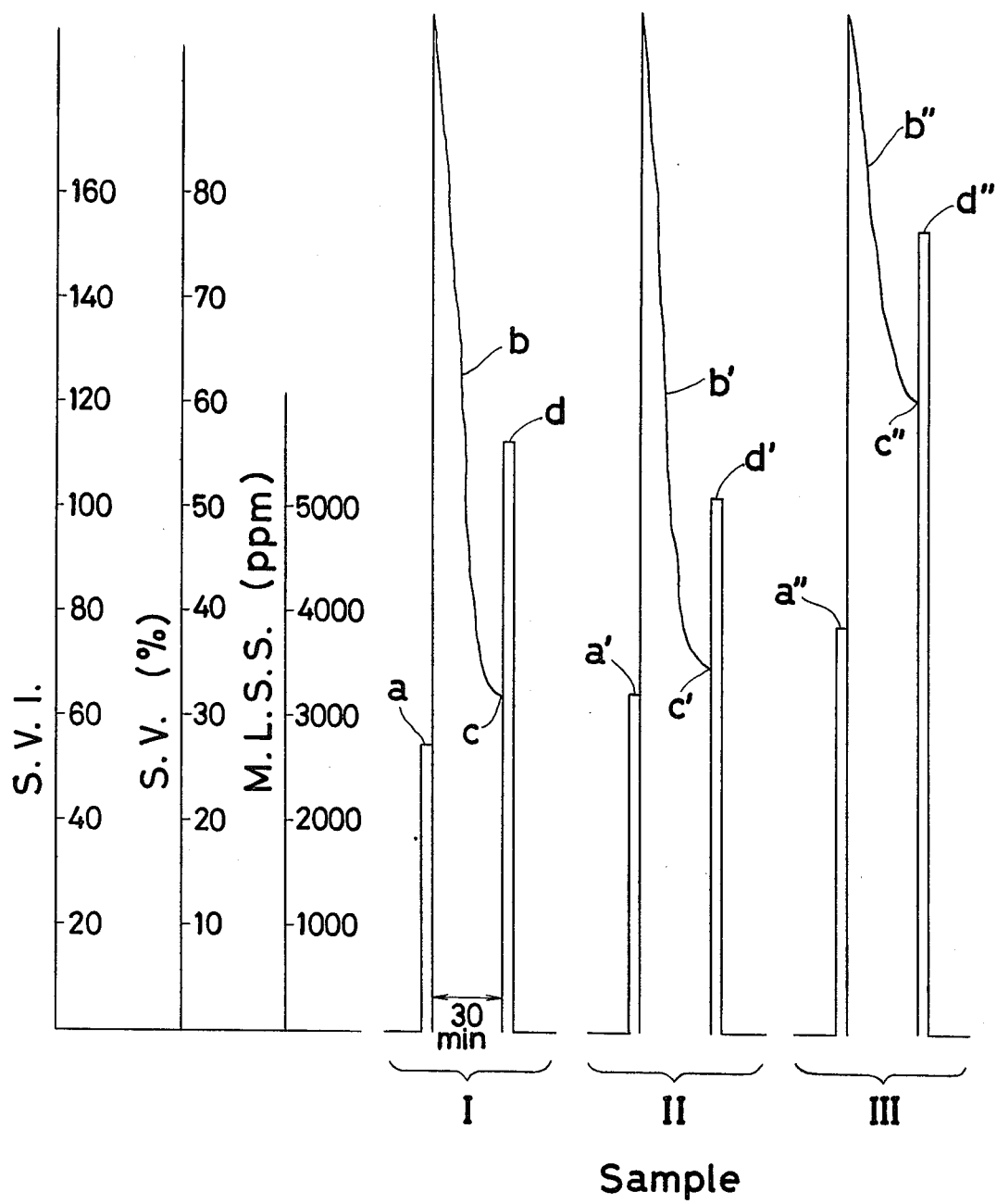
FIG. 5 is a graph showing the automatically determined data of concentration of activated sludge, sedimentation curves of activated sludge, sedimentation rate of activated sludge and S.V.I., obtained of the mixed liquor of activated sludge in the activated sludge process employed in the treatment of an wastewater from a phenol synthesis plant.

At the outlet of the aerator of the wastewater treatment system utilizing the activated sludge process at a phenol synthesis plant, samples were obtained and were subjected to automatic determination of the S.V.I. in accordance with the method described in the specification. The test cell had an inner volume of 100 ml, the angle at which the optical axis of the transmitting light detector and that of the scattering light detector intersected each other was 30° and the time of sedimentation of activated sludge was 30 minutes. Samples were collected and subjected to determination automatically three times. One cycle of determination required about 45 minutes of time. The results were as shown in FIG. 5. The state in which the data were displayed on the digital panel was shown in Table 1.

In FIG. 5, $a$, $a'$ and $a''$ represent the values of concentration of activated sludge (M.L.S.S.) respectively of the samples I, II and III, $b$, $b'$ and $b''$ the respective curves of activated sludge sedimentation, $c$, $c'$ and $c''$ the respective sedimentation rates of activated sludge (S.V.) and $d$, $d'$ and $d''$ the respective values of S.V.I.

Table 1

| Sample No. | M.L.S.S. (ppm) | S.V. (%) | S.V.I. |
|---|---|---|---|
| I | 2,800 | 33 | 117 |
| II | 3,310 | 35 | 105 |
| III | 3,900 | 61 | 156 |

Generally it is held that the treatment in the aerator is proceeding under favorable conditions so far as the values of activated sludge volume index remain in the range of from 60 to 120. It is plain from the preceding table that the condition of separation of the sludge from the treated water was gradually degraded.

What is claimed is:

1. An apparatus for the determination of the activated sludge volume index, which comprises, in combination, means for metering and introducing into a test cell a mixed liquor of activated sludge sampled at the outlet of the aerator or in the final settler, means for blowing air into the test cell for thereby agitating the sample uniformly, means for determining the intensity of transmitting light and the intensity of scattering light in the sample, calculating the logarithm of the ratio of said intensity of scattering light to said intensity of transmitting light and thereby determining the concentration of activated sludge, means for optically following the sedimentation interface of activated sludge in the sample and determining the sedimentation rate of activated sludge within a fixed length of time, an arithmetic circuit adapted to calculate the activated sludge volume index on the basis of the concentration of activated sludge and the sedimentation rate of activated sludge, washing means for discharging the used sample from the test cell and washing the interior of the test cell and automatic process control means for automatically and continuously operating said means for introducing and metering the sample, said means for agitating the sample in the test cell, said means for determining the concentration of activated sludge, said means for determining the sedimentation rate of activated sludge, said arithmetic circuit and said washing means, whereby the activated sludge volume index is automatically determined, displayed, recorded and transmitted.

2. The apparatus according to claim 1, wherein said means for the determination of the concentration of activated sludge comprises a light source and a transmitting light detector disposed opposite each other across the test cell, a scattering light detector disposed in such a position that the optical axis thereof intersects the common optical axis of said light source and said transmitting light detector at the center of said test cell at an angle of about 5 to about 45°, and an arithmetic circuit for calculating the logarithm of the ratio of the intensity of scattering light to the intensity of transmitting light detected by said respective detectors.

3. An apparatus for use in the determination of the activated sludge volume index, which comprises, in combination, a transparent test cell for holding a sample of a mixed liquor of activated sludge, a light source, a transmitted light detector, and a scattered light detector, a support for holding such light source and detectors in a common plane and means restraining motion of said support in said common plane but guiding and permitting positioning said support at a level along the test cell in a direction perpendicular to said common plane for determining the intensity of transmitted light and the intensity of scattered light in the sample for determining the concentration of activated sludge, said means further guiding movement of said support for continuously optically following the sedimentation interface of activated sludge in the sample as it sediments and permittting holding the platform in position for determining the sedimentation rate of activated sludge within a fixed length of time, the light source establishing a beam of dimensions sufficiently small in respect to the dimensions of the test cell as to permit the detection of light scattered by the sample unaffected by transmitted light.

4. The apparatus according to claim 1, wherein said light source and detectors for determination of the concentration of activated sludge comprises a light source and a transmitting light detector disposed opposite each other across the test cell, a scattering light detector disposed in such a position that the optical axis thereof intersects the common optical axis of said light source and said transmitting light detector at the center of said test cell at an angle of about 5° to about 45°.

* * * * *